(12) United States Patent
Degré et al.

(10) Patent No.: US 7,968,320 B2
(45) Date of Patent: Jun. 28, 2011

(54) STABILIZED LIQUID YEAST PREPARATION, A METHOD FOR PRODUCING THE SAME, AND THE USE THEREOF

(75) Inventors: Richard Degré, Quebec (CA); Kevin Kraus, Tenafly, NJ (US); Zhigen Zhang, Notre-Dame-De-Grace (CA)

(73) Assignee: Lallemand USA, Inc., Montreal (CA)

( * ) Notice: Subject to any disclaimer, the term of this patent is extended or adjusted under 35 U.S.C. 154(b) by 0 days.

(21) Appl. No.: 11/474,058

(22) Filed: Jun. 23, 2006

(65) Prior Publication Data

US 2007/0092602 A1    Apr. 26, 2007

Related U.S. Application Data

(60) Provisional application No. 60/694,098, filed on Jun. 24, 2005.

(51) Int. Cl.
  *C12P 7/06*    (2006.01)
(52) U.S. Cl. ............... 435/161; 435/255.1; 435/255.2
(58) Field of Classification Search ............... None
  See application file for complete search history.

(56) References Cited

U.S. PATENT DOCUMENTS

| | | | |
|---|---|---|---|
| 3,993,783 A * | 11/1976 | Langejan et al. | 426/18 |
| 4,755,468 A | 7/1988 | Jung et al. | |
| 6,033,887 A | 3/2000 | Charpentier | |

FOREIGN PATENT DOCUMENTS

| | | |
|---|---|---|
| EP | 0461725 | 12/1991 |
| GB | 1425979 | 2/1976 |
| WO | WO 91/12315 | 8/1991 |
| WO | WO99/55439 | 11/1999 |

OTHER PUBLICATIONS

Myers et al., Applied & Environmental Microbiology, Jan. 1997, p. 145-150.*
Torres et al., Journal of Applied Microbiology, 2003, vol. 94, p. 330-339.*
Jin et al., Applied & Environmental Microbiology, Jan. 2003, vol. 69, No. 1, p. 495-503.*
Mullins, JT, Biotechnology and Bioengineering 1985, vol. 27, p. 321-326.*
Panchal et al. , Biotechnology Letters, 1982, vol. 4, No. 10, p. 639-644.*
Guido et al., Food Chemistry, 2004, vol. 87, p. 187-193.*
Myers et al., Food Microbiology, 1998, vol. 15, p. 51-58.*
Demuyakor et al., Appl. Microbiol. Biotechnol., 1992, vol. 36, p. 717-712.*
Cheong et al., Biotechnology Techniques, 1993, vol. 7, No. 12, p. 879-884.*
Myers et al., Food microbiology, 1999, vol. 16, p. 45-51.*
Dodic et al, "Effects of hydrophilic hydrocolloids on dough and bread performance of samples made from frozen doughs", J. of Food Science, 2007, 72 (4):235-241.
Gugerli et al, "Immobilization as a tool to control fermentation in yeast-leavened refrigerated dough", 2004, Food Hydrocolloids, 18:703-715.

* cited by examiner

*Primary Examiner* — Kade Ariani
(74) *Attorney, Agent, or Firm* — Nutter McClennen & Fish LLP; George A. Xixis; Christopher J. Stow

(57) ABSTRACT

The present invention relates to a novel stabilized liquid yeast preparation which contains a polyhydroxy compound, preferably glycerol, and a gum, comprising carob, guar, tragacanth, arabic or xanthan gum, preferably xanthan gum. The invention also relates to a method for producing said preparation as well as the use of the same.

19 Claims, 3 Drawing Sheets

STABILIZED LIQUID YEAST PREPARATION, A METHOD FOR PRODUCING THE SAME, AND THE USE THEREOF

RELATED APPLICATIONS

This application claims the priority of U.S. Provisional Patent Application Ser. No. 60/694,098, the entire disclosure of which is specifically incorporated herein by reference.

FIELD OF THE INVENTION

The present invention relates to a novel stabilized liquid yeast preparation which contains a polyhydroxy compound, preferably glycerol, and a gum, comprising carob, guar, tragacanth, arabic or xanthan gum, preferably xanthan gum. The invention also relates to a method for producing said preparation as well as the use of the same.

BACKGROUND OF THE INVENTION

Production of fuel ethanol has significantly gained in popularity in the last few years. Nowadays more than 80 such plants are in operation in the USA alone. This enthusiasm has been driven by the need for a replacement for MTBE and the desire to become less energy-dependant on other countries. A typical ethanol production plant will use yeast (typically *Saccharomyces*) to produce an average of 50 millions gallons of pure ethanol per year, mostly but not exclusively from hydrolyzed corn starch in large fermentors of more than 2 millions liters.

The basic carbon and energy sources for yeast growth are sugars. Unmodified starch can not be used because yeast does not contain the appropriate enzymes to hydrolyze this substrate to fermentable sugars. Beet and cane molasses are commonly used as raw material in fermentation because the sugars present in molasses, a mixture of sucrose, fructose and glucose, are readily fermentable. In addition to sugar, yeast also require certain minerals, vitamins and salts for growth. Some of these can be added to the blend of beet and cane molasses prior to flash sterilization while others are fed separately to the fermentation. Alternatively, a separate nutrient feed tank can be used to mix and deliver some of the necessary vitamins and minerals. Required nitrogen is supplied in the form of ammonia and phosphate is supplied in the form of phosphoric acid. Each of these nutrients is fed separately to the fermentation to permit better pH control of the process. The sterilized molasses, commonly referred to as mash or wort, is stored in a separate stainless steel tank. The mash stored in this tank is then used to feed sugar and other nutrients to the appropriate fermentation vessels.

In high volume commercial ethanol production, corn starch is the substrate of choice, because of its low cost and availability. In using corn starch, often a first partial hydrolysis step (using alpha-amylase) precedes a co-saccharification fermentation step (in the presence of glucoamylase) which is then followed by distillation.

A yeast preparation is used to inoculate various fermentors, including so called propagators, usually this occurs at the co-saccharification fermentation stage. The co-saccharification fermentation insures a controlled and progressive hydrolysis of the dextrins produced in the previous partial hydrolysis step. This simultaneous hydrolysis and fermentation provides for a slow release of sugars and insures that the yeast is not exposed to a punctual, very large, osmotic pressure that would exist if all the dextrins had already been hydrolyzed at the beginning of the fermentation and prior to yeast inoculation.

The production of yeast for use in commercial fermentation is, in itself, a multi-step process. In many cases, commercial production requires that the yeast be packaged, stored and shipped in large quantities in a manner that guarantees the purity and viability of the final yeast product.

Baker's yeast production, for example, often starts with a pure culture tube or frozen vial of the appropriate yeast strain. This yeast serves as the inoculum for the pre-pure culture tank, a small pressure vessel where seed is grown in medium under strict sterile conditions. Following growth, the contents of this vessel are transferred to a larger pure culture fermentor where propagation is carried out with some aeration, again under sterile conditions. These early stages are conducted as set-batch fermentations. In set-batch fermentation, all the growth media and nutrients are introduced to the tank prior to inoculation.

From the pure culture vessel, the grown cells are transferred to a series of progressively larger seed and semi-seed fermentors. These later stages are conducted as fed-batch fermentations. During fed-batch fermentation, molasses, phosphoric acid, ammonia and minerals are fed to the yeast at a controlled rate. This rate is designed to feed just enough sugar and nutrients to the yeast to maximize multiplication and prevent the production of alcohol. In addition, these fed-batch fermentations are not completely sterile. It is not economical to use pressurized tanks to guarantee sterility of the large volumes of air required in these fermentors or to achieve sterile conditions during all the transfers through the many pipes, pumps and centrifuges. Extensive cleaning of the equipment, steaming of pipes and tanks, and filtering of the air is practiced to insure as aseptic conditions as possible.

At the end of the semi-seed fermentation, the contents of the vessel are pumped to a series of separators that separate the yeast from the spent molasses. The yeast is then washed with cold water and pumped to a semi-seed yeast storage tank where the yeast cream is held at approximately 34 degrees Fahrenheit until it is used to inoculate the commercial fermentation tanks. These commercial fermentors are the final step in the fermentation process and are often referred to as the final or trade fermentation.

Trade fermentations are carried out in large fermentors with working volumes up to 50,000 gallons. To start the commercial fermentation, a volume of water, referred to as set water, is pumped into the fermentor. Next, in a process referred to as pitching, semi-seed yeast from the storage tank is transferred into the fermentor. Following addition of the seed yeast, aeration, cooling and nutrient additions are started to begin the 15-20 hour fermentation. At the start of the fermentation, the liquid seed yeast and additional water may occupy only about one-third to one-half of the fermentor volume. Constant additions of nutrients during the course of fermentation bring the fermentor to its final volume. The rate of nutrient addition increases throughout the fermentation because more nutrients have to be supplied to support growth of the increasing cell population. The number of yeast cells increase about five- to eight-fold during this fermentation.

Air is provided to the fermentor through a series of perforated tubes located at the bottom of the vessel. The rate of airflow is about one volume of air per fermentor volume per minute. A large amount of heat is generated during yeast growth and cooling is accomplished by internal cooling coils or by pumping the fermentation liquid, also known as broth, through an external heat exchanger. The addition of nutrients and regulation of pH, temperature and airflow are carefully monitored and controlled by computer systems during the entire production process. Throughout the fermentation, the temperature is kept at approximately 86 degrees Fahrenheit and the pH is generally in the range of 4.5-5.5.

At the end of fermentation, the fermentor broth is separated by nozzle-type centrifuges, washed with water and re-centrifuged to yield a yeast cream with a solids concentration of 15 to 24%, and often in the 18% range. The yeast cream is cooled to about 45 degrees Fahrenheit and stored in a separate, refrigerated stainless steel cream tank. Cream yeast can be loaded directly into tanker trucks and delivered to customers equipped with an appropriate cream yeast handling system. Alternatively, the yeast cream can be pumped to a plate and frame filter press and dewatered to a cake-like consistency containing 27-33% yeast solids. This press cake yeast is crumbled into pieces and packed into 50-pound bags that are stacked on a pallet. The yeast heats up during the pressing and packaging operations and the bags of crumbled yeast must be cooled in a refrigerator for a period of time with adequate ventilation and placement of pallets to permit free access to the cooling air. Palletized bags of crumbled yeast are then distributed to customers in refrigerated trucks. Cream yeast can also be further processed into dried yeast (92-97% solids) by using a fluid bed dryer or similar types of dryers.

In contrast, yeast production for fuel ethanol plants is significantly different. Even though fuel ethanol plants are very large, they consume much less yeast than industrial bakeries. A large industrial bakery, for example, will take anywhere between 1 and 4 to 5 truckloads of 20,000 liters of cream yeast (average of 18% solids) per week. It is therefore common to see cream yeast systems installed at those bakeries; they are usually comprised of two large refrigerated, agitated receivers that can receive at least one truckload of liquid yeast each, a distribution ring to the dough mixers and a full cleaning in place (CIP) system. By analogy, a large fuel ethanol plant will typically use 200 to 500 kg of dry yeast per week or the equivalent of 1500 to 2500 liters of cream yeast per week. Such a reduced usage, however, cannot justify installing sophisticated cream yeast systems that are common in the baking industry.

Fuel ethanol plants, in contrast, use dry yeast and a series of propagation tanks to multiply and activate the yeast. The use of such propagation tanks reduces the amount of yeast required and effectively eliminates the need for refrigerated storage. Dry yeast has the additional benefit of having a relatively long shelf life (up to about 3 months). Unfortunately, dry yeast loses part of its fermentative activity during the drying process as well as during rehydration. Moreover, dry yeast is in a dormant state (hence the propagation step commonly seen in fuel ethanol plants) and is not as fast as fresh yeast (27-33% solids).

The ethanol industry has also been using fresh yeast but fresh compressed or crumbled yeast requires refrigeration for storage and has an average storage life is 2 to 3 weeks. Compressed yeast can of course be kept for longer period of time (up to 6 weeks) but this results in a significant loss of activity and also allows for the possibility development of molds on the surface of the yeast. Liquid cream yeast (15 to 24%) suffers the same aging and refrigeration problem and requires agitation because of the natural tendency of yeast to sediment.

None of the above-mentioned forms in which yeast is currently supplied is fully satisfactory. The rather small quantities of yeast required in commercial ethanol facilities, as compared to the size of the operations, does not make it economical to deliver small amount of yeast on a frequent basis to those plants. In many cases, fresh yeast may not be available or the fresh compressed yeast may become dry, moldy or inactive. Conversely, a dry yeast product remains active for a long period of time but, in any case, it must be awakened properly and is not as fast as fresh yeast; this is one of the main reasons why propagators are common in the industry. As to cream yeast, it has the tendency to sediment to the bottom of the container in which it is transported. Consequently the cream yeast has to be stirred before use.

Thus the present invention aims at eliminating the disadvantages described above.

SUMMARY OF THE INVENTION

One of the objects of the present invention is to provide a novel, easily batched, stabilized liquid yeast (SLY) preparation that doesn't require agitation, having an improved shelf life over standard liquid yeast of up to 90 days.

Another object is to provide a stabilized liquid high activity yeast preparation having a shorter lag phase and a better overall performance than the corresponding compressed yeast.

A further object of the invention is to provide a stabilized liquid yeast preparation for direct pitching of production fermentors for alcohol production, therefore bypassing the propagation step, as suggested by the shorter lag phase.

The above-mentioned objects are achieved by the novel method of producing a stabilized liquid yeast preparation by using a combination of a polyhydroxy compound, preferably glycerol and a gum, preferably xanthan gum. The glycerol stabilizes yeast vitality and xanthan gum stabilizes consistency, preventing yeast settling.

A further object of the invention is the use of Stabilized Liquid Yeast to produce commercial quantities of high activity and/or high budding yeast. In particular, what is contemplated is a formulation comprising a high nitrogen, protein, activity or budding yeast together with a gum and a polyhydroxy compound, preferably glycerol.

A further object of the invention is a novel process for the production of ethanol which comprises the direct addition or pitching of a high budding stabilized liquid yeast to a production fermentor, thereby obviating the need for a propagation step.

DETAILED DESCRIPTION OF THE INVENTION

Figure 1:
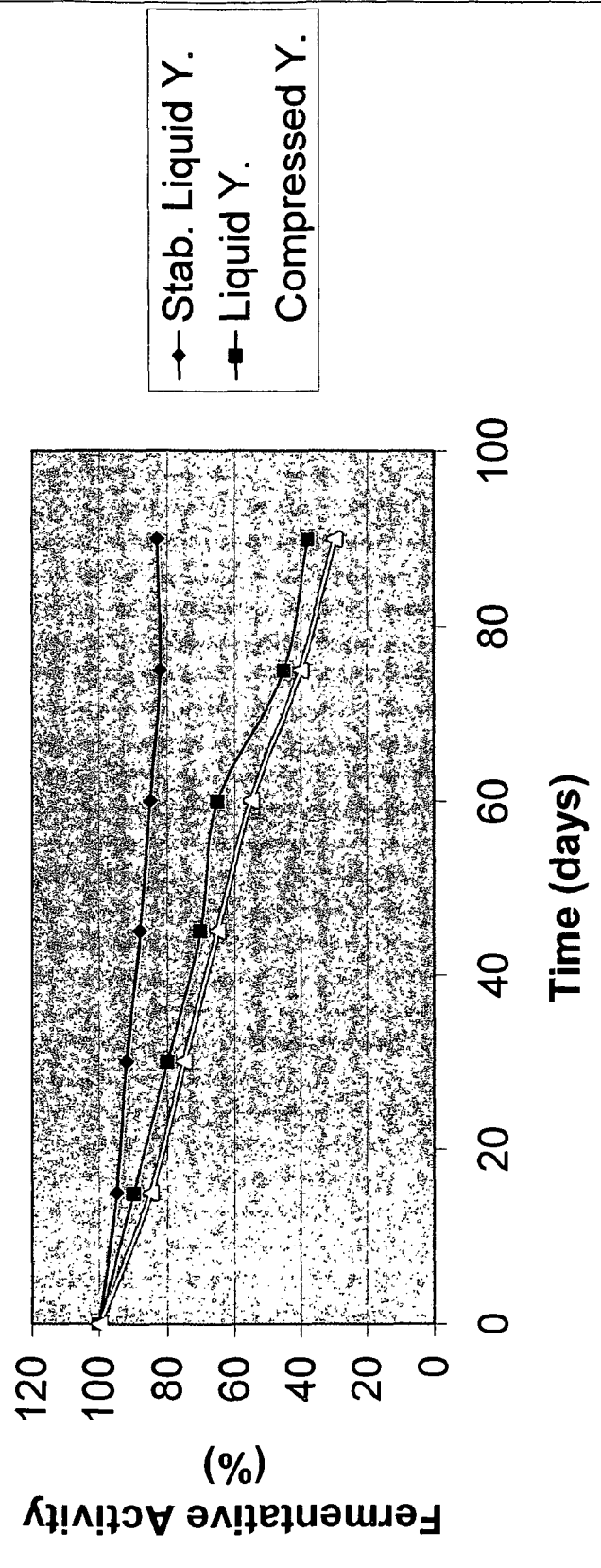
FIG. 1 illustrates the relative fermentative activity of a stabilized liquid yeast preparation against that of bags (compressed yeast) and that of regular liquid yeast.

Fresh yeast, whether it is in liquid (cream) form or in pressed or crumbled form, has a number of benefits. Such yeast is optimized for activity, does not require rehydration, and has a shorter lag phase in the fermentor. Fresh yeast is generally used for strains that cannot tolerate drying.

Dry yeast, whether active or inactive, has a set of different benefits. It is generally optimized for stability, does not require refrigeration and is good for intermittent use (continuous fermentation start-up). It is generally used for strains that are used in small volumes.

What is needed therefore is s Stabilized Liquid Yeast (SLY) that has many of the benefits of both liquid yeast and dry yeast. In particular what is necessary is a yeast formulation that has greater activity than conventional fresh yeast; greater stability than conventional fresh yeast; a shorter lag phase in the fermentor; does not require agitation; and provides for the possibility of direct pitching without the necessity of a propagator.

The present invention provides for an SLY that fulfills these unmet needs. The SLY of the invention is comprised of a liquid or cream yeast, in combination with one or more gums and one or more polyhydroxy compounds.

More specifically, the invention comprises a cream or liquid yeast (15-24% solids), which further comprises a gum and a polyhydroxy compound. The gum is suitably present in the cream yeast in a concentration of 0.03 to 1% by weight of the cream yeast, and is preferably carob, guar, tragacanth, arabic or xanthan gum. The term gum includes gums which can be obtained from plants or which are of microbial origin or mixtures thereof.

The formulation of the invention also includes one or more polyhydroxy compounds. Preferred polyhydroxy compounds are propylene glycol, glycerol, non-fermentable mono- or oligosaccharides, such as xylose, or non-fermentable sugar alcohols, such as mannitol and sorbitol, soluble oligo- or polymeric carbohydrates such as partially hydrolyzed starch, cellulose or agarose and polyethylene glycol or mixtures thereof. Preferably the invention contains 1 to 5% glycerol by weight of cream yeast.

In a most preferred embodiment 0.5 g/kg of mash of SLY is used in fermentation wherein the SLY is comprised of 3.2% (w/v) of 95% glycerol and 0.1% (w/v) of xanthan gum.

Furthermore, the present invention contemplates a Stabilized Liquid Yeast formulation wherein the yeast is a high nitrogen, protein, activity or budding yeast. Such high activity or budding include, but are not limited to living yeast cells such as from the genera *Saccharomyces, Kluyveromyces, Torulaspora*, in particular *Saccharomyces cerevisiae*. The term also comprises combinations of one or more yeast species.

A further object of the invention is a novel process for the production of ethanol, comprising the direct addition or pitching of a high budding stabilized liquid yeast to a production fermentor, thereby obviating the need for a propagation step.

Such stabilized liquid yeast preparations are not only of interest for the fuel ethanol industry (not limited to corn mash fermentation either, but also including 'biomass' or cellulosic substrates or any other substrates used in the manufacturing of fuel ethanol) but are also applicable to potable alcohols (distilling), brewing, baking, fermented beverages in general, and any fermentations process requiring the characteristics of said stabilized liquid yeast.

Processing aids can be added to the compositions of the invention in such an amount that the properties of the final product are improved when said compositions are added to the fermenting mixture or dough. As described below the processing aids can be divided into nutrients, chemical additives and enzymes.

Nutrient components can include inorganic nitrogen (such as urea and nitrogen salts), organic nitrogen (such as yeast, yeast autolysate, yeast extract, or fermentation solubles), phosphorous (such as salts of nitrogen and phosphorous), minerals (as salts), vitamins.

Suitable chemical additives are oxidizing agents such as ascorbic acid, bromate and azodicarbonamide and/or reducing agents such as L-cysteine and glutathione. A preferred oxidizing agent often used for baking is ascorbic acid, which is added to the composition in such amounts that result in an amount between 5 and 300 mg per kg flour. Other suitable chemical additives are emulsifiers acting as dough conditioners such as diacetyl tartaric esters of mono/diglycerides (DATEM), sodium stearoyl lactylate (SSL) or calcium stearoyl lactylate (CSL), or acting as crumb softeners such as glycerol monostearate (GMS) or bile salts, fatty materials such as triglycerides (fat) or lecithin and others. Preferred emulsifiers are DATEM, SSL, CSL or GMS. Preferred bile salts are cholates, deoxycholates and taurodeoxycholates.

Suitable enzymes are starch degrading enzymes, arabinoxylan- and other hemicellulose degrading enzymes, cellulose degrading enzymes, oxidizing enzymes, fatty material splitting enzymes, protein degrading enzymes. Preferred starch degrading enzymes are endo-acting amylases such as alpha-amylase and exo-acting amylases such as beta-amylase and glucoamylase. Preferred arabinoxylan degrading enzymes are pentosanases, hemicellulases, xylanases and/or arabinofuranosidases, in particular xylanases from *Aspergillus* of *Bacillus* species. Preferred cellulose degrading enzymes are cellulases (i.e. endo-1,4-beta-glucanases) and cellobiohydrolasesi in particular from *Aspergillus, Trichoderma* or *Humicola* species. Preferred oxidizing enzymes are lipoxygenases, glucose oxidases, sulfhydryl oxidases, hexose oxidases, pyranose oxidases and laccases. Preferred fatty material splitting enzymes are lipases, in particular fungal lipases from *Aspergillus* or *Humicola* species, and phospholipases such as phospholipase A1 and/or A2. Preferred protein degrading enzymes are endo-acting proteinases such as those belonging to the classes thiolproteases, metalloproteases, serine proteases and aspartyl proteases, as well as exo-acting proteinases, also referred to as peptidases, belonging to the class of aminopeptidases and carboxypeptidases. Additionally, microbial and plant proteases for producing free amino nitrogen from the proteins in grain can also be added.

The enzymes may originate from animal, plant or microbial origin and they may be obtained from these sources by classical processes known in the art, or, alternatively, they may be produced via recombinant DNA technology. A preferred production process comprises fermentation processes in which fungi, yeast or bacteria are grown and produce the desired enzymes, either inherently or as a result of genetic modification (recombinant DNA technology). These processes are well known in the art. Preferably, the enzymes are secreted by the micro-organisms into the fermentation broth. At the end of the fermentation process, the cell biomass is usually separated and, depending on the enzyme concentration in the broth, the latter may be concentrated further and optionally washed by known techniques such as ultrafiltration. Optionally, the enzyme concentrates or a mixture of such concentrates may be dried by known techniques such as spray drying.

The invention is not restricted to any specific type of yeast and, in particular, the invention is not restricted to a SLY formulation wherein the yeast is Saccharomyces. In fact, it would be obvious to one ordinary skill in the art that the invention would include all types of yeast as well as bacteria used in commercial fermentation processes including bacteria used in the production of ethanol.

Furthermore, although the invention contemplates the use of said Stabilized Liquid Yeast preparation in commercial fermentors, it is not so limited. The SLY but may be added at any step of the process, including to the propagators.

EXAMPLES

Corn Mash and Yeast Samples

Industrial corn mash was used in all the bench scale comparative fermentation tests. The mash already had the backset added. It is about 60% of the liquid used to make the mash. The mash was made from the corn from South Dakota and has been jet cooked to 130° C. for 2 minutes. The corn mash was taken just after liquefaction. No glucoamylase or urea were added in the mash. Corn mash total solids were determined to be about 30%.

Yeast used is a fuel ethanol strain of Saccharomyces cerevisiae produced by Lallemand Inc and distributed by Ethanol Technology. Compressed yeast was made from the same strain.

Flask Mash Fermentation Experiments

Standard lab corn mash fermentation protocol was used. 100 g of the industrial corn mash as described above was accurately dispensed into 125 ml Erlenmeyer flasks. To each flask, 20 μm glucoamylase and 16 mM urea were added. For the experiments, the pitching rate was 0.5 g/kg (As Is). The IDY yeast samples were first rehydrated in tap water at 37° C. for 15 minutes before inoculation. After inoculating each flask, the corn mash fermentations were conducted in a rotation shaker at 35° C. and 150 rpm. All the shaker flask experiments were conducted in triplicates.

The foundation of the gravimetric method is based on the weight loss during the corn mash fermentation. During the fermentation carbon dioxide is produced and released, resulting in the weight loss in the jar or flask. Then the ethanol production is determined based on the stoichiometric relationship between the carbon dioxide and ethanol. By recording the weight loss at certain interval during the fermentation, ethanol production rate and yield can be determined. The gravimetric method provides a reliable, convenient and cheap method for ethanol determination.

Example 1

Stability Test Shelf Life Comparison

The stability and shelf life of Stabilized Liquid Yeast was compared to traditional Liquid Yeast and Compressed Yeast products. Fermentation Activity was measured by the gravimetric method. Yeast used is a fuel ethanol strain of Saccharomyces cerevisiae produced by Lallemand Inc. and distributed by Ethanol Technology. Activity was measured by gravimetric method.

As shown in the table below and in FIG. 1, the stabilized preparation has a better shelf life and shows no sign of significant settling.

TABLE 1

Shelf Life Comparison

| Time (days) | Stabilized Liquid Yeast | Liquid (Cream) Yeast | Compressed Yeast |
|---|---|---|---|
| | Fermentative Activity (%) | | |
| 0 | 100 | 100 | 100 |
| 15 | 95 | 90 | 85 |
| 30 | 92 | 80 | 75 |
| 45 | 88 | 70 | 65 |
| 60 | 85 | 65 | 55 |
| 75 | 82 | 45 | 40 |
| 90 | 83 | 38 | 30 |

Example 2

Comparative Performance of SLY Yeast Ethanol Production

A comparison of the ethanol production capability of active dry yeast, compressed yeast and stabilized liquid yeast was performed. As mentioned above, all yeast used in this experiment is a fuel ethanol strain of *Saccharomyces cerevisiae* produced by Lallemand Inc and distributed by Ethanol Technology. Activity measured by gravimetric method described above. The stabilized liquid yeast tested was comprised of 3.2% (w/v) of 95% Glycerol and 0.1% (w/v) of Xanthan gum.

Figure 2:
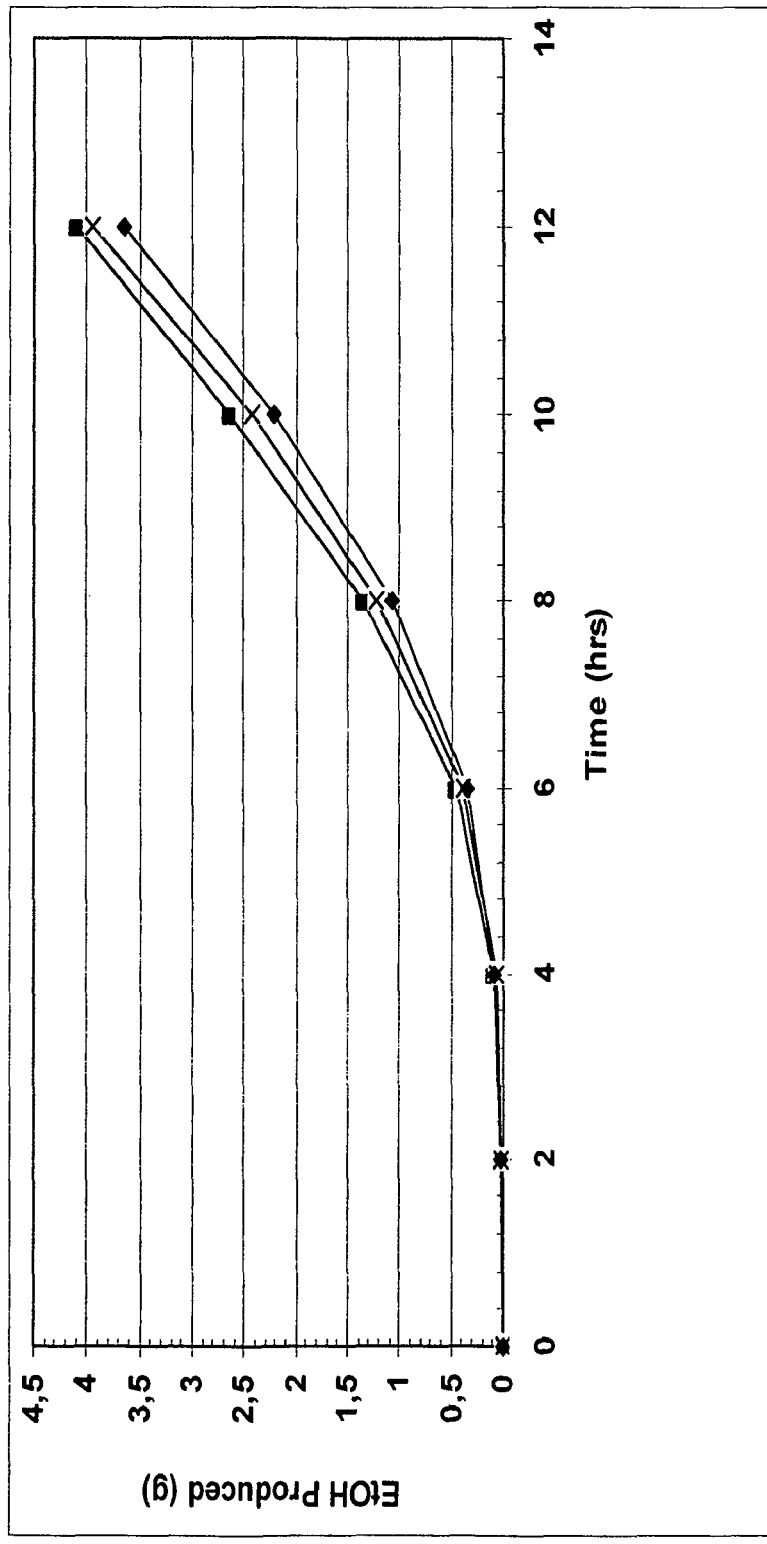
FIG. 2 illustrates the better performance of a stabilized liquid yeast preparation against regular compressed yeast and dry yeast during the first 12 hours of corn mash fermentation.

Yeast was incubated with corn mash and production of ethanol was measured at 2 hour intervals for 12 hours. Table 2 and FIG. 2 show that SLY had a faster fermentation role than either compressed yeast or active dry yeast.

The corn mash is of industrial origin, contains 60% backset and has already been treated with alpha-amylase. See above. It illustrates how glycerol contributes to stabilize the vitality of "very active" yeast that in turns translates into a shorter lagphase. Although the invention covers yeast in every physiological state (exponential phase of growth, stationary phase of growth, etc), the term "very active" yeast means yeast with more than 3% budding cells or/and yeast with a protein content (N×6.25) greater than 40%) and with/or a phosphate (as $P_2O_5$) content greater than 2%. This shorter lagphase also contributes to reduce the impact of inherent bacterial contamination coming with the mash and allow the fuel ethanol producer to bypass the propagation step and to add the yeast (pitching step) directly to the fermentors. It may also contribute to reduce the use of antibiotics commonly used in this industry.

TABLE 2

Comparative Performance of SLY yeast during first 12 hours of fermentation

| | | 2 H | | | 4 H | | | 6 H | | |
|---|---|---|---|---|---|---|---|---|---|---|
| | weight (g) | weight (g) | weight loss | EtOH Produced (g) | weight | weight loss | EtOH Produced (g) | weight | weight loss | EtOH Produced (g) |
| Dry Yeast | 213.12 | 213.1 | 0.02 | 0.0209 | 213.06 | 0.06 | 0.0627 | 212.8 | 0.32 | 0.3344 |
| | 216.37 | 216.35 | 0.02 | 0.0209 | 216.29 | 0.08 | 0.0836 | 216.02 | 0.35 | 0.36575 |
| | 219.18 | 219.14 | 0.04 | 0.0418 | 219.1 | 0.08 | 0.0836 | 218.84 | 0.34 | 0.3553 |
| SLY | 216.52 | 216.49 | 0.03 | 0.03135 | 216.43 | 0.09 | 0.09405 | 216.1 | 0.42 | 0.4389 |
| | 213.9 | 213.9 | 0 | 0 | 213.87 | 0.03 | 0.03135 | 213.5 | 0.4 | 0.418 |
| | 214.82 | 214.79 | 0.03 | 0.03135 | 214.71 | 0.11 | 0.11495 | 214.36 | 0.46 | 0.4807 |
| Compressed | 215.08 | 215.05 | 0.03 | 0.03135 | 215.01 | 0.07 | 0.07315 | 214.72 | 0.36 | 0.3762 |
| | 215.3 | 215.28 | 0.02 | 0.0209 | 215.23 | 0.07 | 0.07315 | 214.93 | 0.37 | 0.38665 |
| | 213.73 | 213.71 | 0.02 | 0.0209 | 213.66 | 0.07 | 0.07315 | 213.35 | 0.38 | 0.3971 |

TABLE 2-continued

Comparative Performance of SLY yeast during first 12 hours of fermentation

| | | 8 H | | | 10 H | | | 12 H | | |
|---|---|---|---|---|---|---|---|---|---|---|
| | weight (g) | weight | weight loss | EtOH Produced (g) | weight | weight loss | EtOH Produced (g) | weight | weight loss | EtOH Produced (g) |
| Dry Yeast | 213.12 | 212.1 | 1.02 | 1.0659 | 211.03 | 2.09 | 2.18405 | 209.66 | 3.46 | 3.6157 |
| | 216.37 | 215.3 | 1.07 | 1.11815 | 214.22 | 2.15 | 2.24675 | 212.85 | 3.52 | 3.6784 |
| | 219.18 | 218.17 | 1.01 | 1.05545 | 217.09 | 2.09 | 2.18405 | 215.68 | 3.5 | 3.6575 |
| SLY | 216.52 | 215.27 | 1.25 | 1.30625 | 214.06 | 2.46 | 2.5707 | 212.63 | 3.89 | 4.06505 |
| | 213.9 | 212.63 | 1.27 | 1.32715 | 211.39 | 2.51 | 2.62295 | 209.99 | 3.91 | 4.08595 |
| | 214.82 | 213.48 | 1.34 | 1.4003 | 212.24 | 2.58 | 2.6961 | 210.85 | 3.97 | 4.14865 |
| Compressed | 215.08 | 213.93 | 1.15 | 1.20175 | 212.79 | 2.29 | 2.39305 | 211.34 | 3.74 | 3.9083 |
| | 215.3 | 214.14 | 1.16 | 1.2122 | 212.97 | 2.33 | 2.43485 | 211.54 | 3.76 | 3.9292 |
| | 213.73 | 212.56 | 1.17 | 1.22265 | 211.38 | 2.35 | 2.45575 | 209.93 | 3.8 | 3.971 |

Example 3

Improved Ethanol Yield of Stabilized Liquid Yeast

Figure 3:
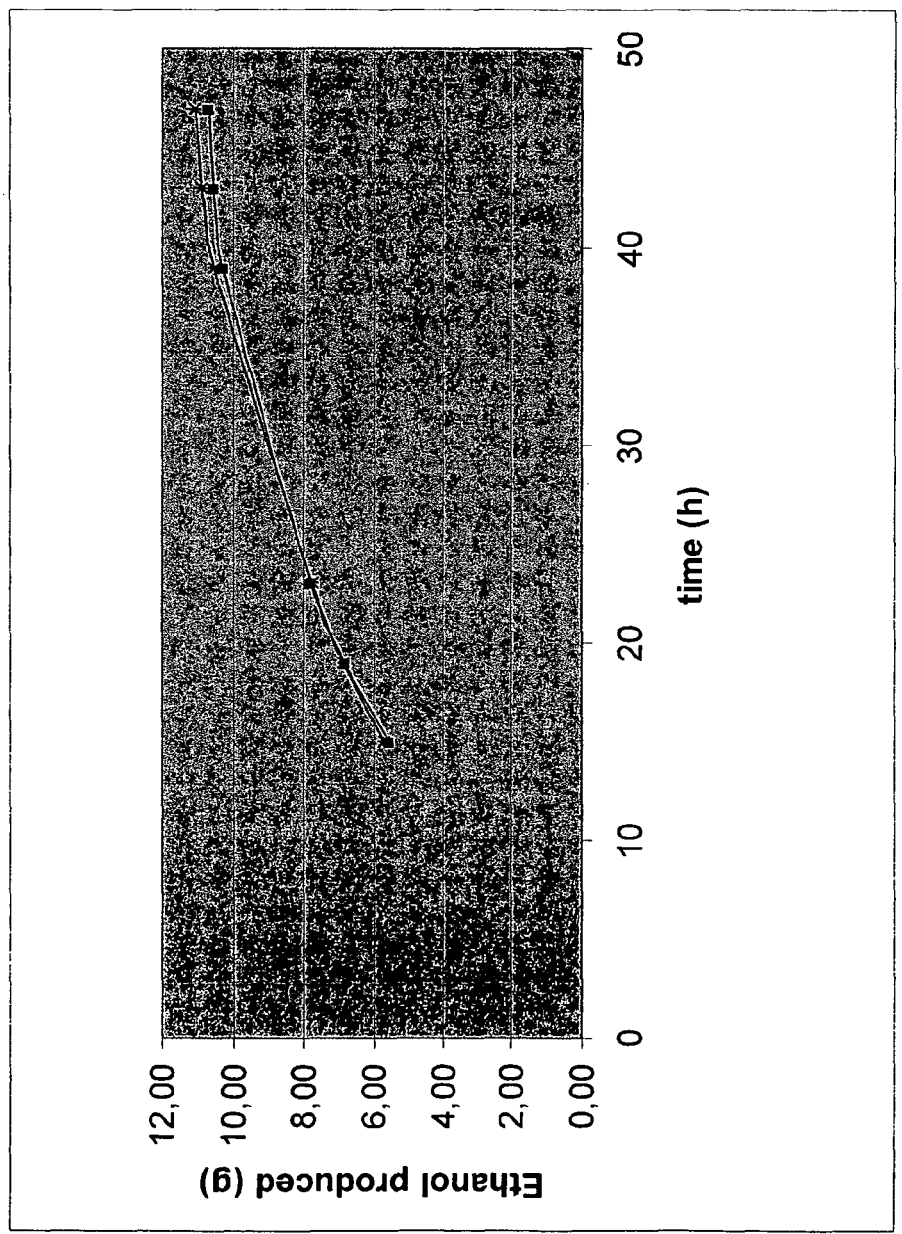
FIG. 3 improved ethanol yield of stabilized liquid yeast over compressed yeast.

Table 3 and FIG. 3 further illustrate how the stabilization process allows a liquid yeast preparation to perform better (i.e. have a better ethanol yield). Stabilized Liquid Yeast was compared to Compressed yeast for the same amount of "as-is" solids. The same corn mash composition as Example 2 was used.

As mentioned above, all yeast used in this experiment is a fuel ethanol strain of Saccharomyces cerevisiae produced by Lallemand Inc and distributed by Ethanol Technology. Activity measured by gravimetric method described above. The stabilized liquid yeast tested was comprised of 3.2% (w/v) of 95% Glycerol and 0.1% (w/v) of Xanthan gum.

It is apparent from the results that the stabilization process allow the yeast to give a better ethanol yield than the un-stabilized form. The slight difference observed translates into dramatic improvement at full industrial scale.

TABLE 3

Improved ethanol yield of Stabilized liquid yeast over compressed yeast

| Sample # | Conc. (g/kg) | Strain | Time | | | | | | | |
|---|---|---|---|---|---|---|---|---|---|---|
| | | | 0 | 15 | 19 | 23 | 39 | 43 | 47 | 63 |
| | | | MASS OF FLASKS | | | | | | | |
| 1 | 0.25 | SLY | 215.12 | 209.56 | 208.53 | 207.63 | 204.96 | 204.70 | 204.54 | 204.36 |
| 2 | 0.25 | SLY | 216.50 | 211.03 | 209.90 | 209.06 | 206.45 | 206.16 | 205.96 | 205.66 |
| 3 | 0.25 | SLY | 219.46 | 213.89 | 212.79 | 211.93 | 209.35 | 209.11 | 208.91 | 208.70 |
| 4 | 0.25 | Compressed | 213.98 | 208.60 | 207.29 | 206.32 | 204.01 | 203.85 | 203.72 | 203.53 |
| 5 | 0.25 | Compressed | 203.66 | 198.36 | 197.12 | 196.20 | 193.81 | 193.59 | 193.44 | 193.18 |
| 6 | 0.25 | Compressed | 219.01 | 213.78 | 212.55 | 211.63 | 209.27 | 209.06 | 208.91 | 208.61 |
| | | | WEIGHT LOSS | | | | | | | |
| 1 | 0.25 | SLY | | 5.56 | 6.59 | 7.49 | 10.16 | 10.42 | 10.58 | 10.76 |
| 2 | 0.25 | SLY | | 5.47 | 6.6 | 7.44 | 10.05 | 10.34 | 10.54 | 10.84 |
| 3 | 0.25 | SLY | | 5.57 | 6.67 | 7.53 | 10.11 | 10.35 | 10.55 | 10.76 |
| 4 | 0.25 | Compressed | | 5.38 | 6.69 | 7.66 | 9.97 | 10.13 | 10.26 | 10.45 |
| 5 | 0.25 | Compressed | | 5.3 | 6.54 | 7.46 | 9.85 | 10.07 | 10.22 | 10.48 |
| 6 | 0.25 | Compressed | | 5.23 | 6.46 | 7.38 | 9.74 | 9.95 | 10.1 | 10.4 |
| | | | ETHANOL PRODUCED | | | | | | | |
| 1 | 0.25 | SLY | | 5.8102 | 6.8866 | 7.8271 | 10.6172 | 10.8889 | 11.0561 | 11.2442 |
| 2 | 0.25 | SLY | | 5.7162 | 6.8970 | 7.7748 | 10.5023 | 10.8053 | 11.0143 | 11.3278 |
| 3 | 0.25 | SLY | | 5.8207 | 6.9702 | 7.8689 | 10.5650 | 10.8158 | 11.0248 | 11.2442 |
| 4 | 0.25 | Compressed | | 5.6221 | 6.9911 | 8.0047 | 10.4187 | 10.5859 | 10.7217 | 10.9203 |
| 5 | 0.25 | Compressed | | 5.5385 | 6.8343 | 7.7957 | 10.2933 | 10.5232 | 10.6799 | 10.9516 |
| 6 | 0.25 | Compressed | | 5.4653 | 6.7507 | 7.7121 | 10.1783 | 10.3978 | 10.5545 | 10.8680 |

Example 4

Comparison of Fermentation Performance after 8 Weeks Storage

As mentioned above, all yeast used in this experiment is a fuel ethanol strain of *Saccharomyces cerevisiae* produced by Lallemand Inc and distributed by Ethanol Technology. Activity measured by gravimetric method described above. The stabilized liquid yeast tested was comprised of 3.2% (w/v) of 95% Glycerol and 0.1% (w/v) of xanthan gum.

TABLE 4

Fermentation Performance after 8 weeks storage

| Time | Fresh Bag Yeast | Stabilized Liquid Yeast |
| --- | --- | --- |
| 6.5 Hours | 0.630 g | 0.664 g |
| 8 Hours | 1.341 g | 1.393 g |
| 10 Hours | 2.633 g | 2.710 g |
| 24 Hours | 8.012 g | 8.085 g |
| 32 Hours | 9.712 g | 9.868 g |
| 48 Hours | 11.007 g | 11.234 g |

Experiment 5

Activity after 8 Weeks Storage

In this experiment, Baker's yeast from Lallemand was used; the SLY was produced using 3.2% of 95% glycerol and 0.1% xanthan gum (all w/v). Under normal stress the yeast was tested in a white pan bread formulation containing, amongst other ingredients, 3.8% (w/w Vs flour) sugar, 1.7% (w/w) of table salt (NaCl), and 181 g of water for 275 g of flour. Under stress conditions the yeast was tested for its gas production in a dough containing 16.7% (w/w Vs flour) sugar (sucrose), 16.7% (w/w Vs flour) fat (shortening), 2% (w/w) of salt and 147 g of water for 300 g of flour.

Gas production was evaluated by putting a known amount of dough into a fermentograph, (SJA (Sweeden) or Risograph (USA)) and incubating it for one hour at 35 C. The same amount of yeast was used in this example; that is 4.7% (w/w Vs flour) of compressed yeast or its equivalent of SLY for the Normal Stress conditions and 5.0% of compressed yeast or its equivalent of SLY under High Stress conditions.

This experiment shows that Stabilized Liquid Yeast outperforms fresh bag yeast after an extended storage period (8 weeks). It also shows that SLY has significantly improved fermentation characteristics in situations of high stress

TABLE 5

Activity Test Results after 8 weeks storage

| Activity Tests | Fresh Bag Yeast | Stabilized Liquid Yeast |
| --- | --- | --- |
| High Stress | 275 cc | 360 cc |
| Normal Stress | 550 cc | 575 cc |

The invention claimed is:

1. A stabilized liquid yeast composition for ethanol production comprising yeast in combination with one or more gums and one or more polyhydroxy compounds,
    wherein the yeast is of a genus *Saccharomyces*, and
    wherein the gum is present at about 0.03 to about 1% by weight of the yeast, and
    wherein the polyhydroxy compound is present at about 1 to 5% by weight of yeast wherein the composition has a fermentative activity of at least 82% after 45 days, and an ethanol yield greater than that of conventional liquid yeast and compressed yeast compositions.

2. The composition of claim 1 wherein the yeast is in the form of cream yeast.

3. The composition of claim 2 wherein the cream yeast is comprised of about 15-24% solids.

4. The composition of claim 1 wherein the gum is selected from the group consisting of carob, tragacanth, Arabic, guar and xanthan gum.

5. The composition of claim 1 wherein the polyhydroxy compound is selected from the group consisting of glycerol, propylene glycol, non-fermentable monosaccharides, non-fermentable oligosaccharides, non-fermentable sugar alcohols, soluble oligo-carbohydrates, soluble polymeric carbohydrates and polyethylene glycol.

6. The composition of claim 5 wherein the non-fermentable monosaccharide is xylose.

7. The composition of claim 5 wherein the non-fermentable sugar alcohol is selected from the group consisting of mannitol and sorbitol.

8. The composition of claim 5 wherein the polymeric carbohydrate is selected from the group consisting of hydrolyzed starch, cellulose and agarose.

9. The composition of claim 1 wherein the yeast is selected from the group comprising high activity yeast, high budding yeast, high nitrogen yeast and high protein yeast.

10. The composition of claim 9 wherein the yeast is high budding yeast.

11. A method of fuel ethanol production comprising directly pitching the composition of claim 1 to a fuel ethanol production fermentor comprising a fermentable substance and fermenting under conditions suitable to produce fuel ethanol.

12. A method of fuel ethanol production comprising directly pitching the composition of claim 10 to a fuel ethanol production fermentor comprising a fermentable substance and fermenting under conditions suitable to produce fuel ethanol.

13. A method of fuel ethanol production comprising combining the composition of claim 1 with a fermentable substance in a fuel ethanol production fermentor and fermenting under conditions suitable to produce fuel ethanol.

14. The composition of claim 1 further comprising a fermentable substance.

15. The composition of claim 14 wherein the fermentable substance is corn mash.

16. The method of claim 13 wherein the fermentable substance is corn mash.

17. The composition of claim 1, wherein the composition provides both greater stability and greater activity compared to conventional liquid yeast and compressed yeast compositions.

18. The method of claim 13, wherein the composition provides both greater stability and greater activity compared to conventional liquid yeast and compressed yeast compositions.

19. A method of stabilizing a yeast composition for fuel ethanol production comprising:
    providing a yeast of genus *Saccharomyces*,
    combining the yeast with a gum and a polyhydroxy compound so as to form a yeast composition,
    wherein the gum is present at about 0.03 to about 1% by weight of the yeast,
    wherein the polyhydroxy compound is present at about 1 to 5% by weight of yeast, and wherein the yeast composition provides greater stability and greater activity compared to conventional liquid yeast and compressed yeast compositions, wherein said composition has a fermentative activity of at least 82% after 45 days, and has an ethanol yield greater than that of conventional liquid yeast and compressed yeast compositions.

* * * * *